US008303532B2

(12) United States Patent
Hamada et al.

(10) Patent No.: US 8,303,532 B2
(45) Date of Patent: Nov. 6, 2012

(54) PERTIONEAL MEMBRANE FUNCTION TEST METHOD, PERITONEAL MEMBRANE FUNCTION TEST APPARATUS AND PERITONEAL MEMBRANE FUNCTION TEST PROGRAM

(75) Inventors: Hiroyuki Hamada, Fukuoka (JP); Masahiro Okamoto, Iizuka (JP); Shinji Namoto, Hatsukaichi (JP); Tomokazu Karino, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 1249 days.

(21) Appl. No.: 12/083,094

(22) PCT Filed: Aug. 22, 2006

(86) PCT No.: PCT/JP2006/316434
§ 371 (c)(1),
(2), (4) Date: Apr. 4, 2008

(87) PCT Pub. No.: WO2007/046186
PCT Pub. Date: Apr. 26, 2007

(65) Prior Publication Data
US 2009/0271119 A1    Oct. 29, 2009

(30) Foreign Application Priority Data
Oct. 18, 2005    (JP) ................................. 2005-302958

(51) Int. Cl.
*A61M 1/00*    (2006.01)
(52) U.S. Cl. .......... 604/29; 210/646; 210/647; 700/271; 424/520

(58) Field of Classification Search .................... 604/29; 210/646–647; 700/271; 424/520
See application file for complete search history.

(56) References Cited

U.S. PATENT DOCUMENTS
5,670,057 A * 9/1997 Chen et al. .................... 210/739
2006/0287585 A1   12/2006 Hamada et al.
2007/0061045 A1   3/2007 Hamada et al.

FOREIGN PATENT DOCUMENTS
| JP | 2000-140100 | 5/2000 |
| JP | 2000-271127 | 10/2000 |
| JP | 2003-275302 | 9/2003 |
| JP | 2004-358230 | 12/2004 |
| JP | 2005-27886 | 2/2005 |

OTHER PUBLICATIONS

International Search Report issued Sep. 26, 2006 in the International (PCT) Application of which the present application is the U.S. National Stage.

* cited by examiner

*Primary Examiner* — In Suk Bullock
*Assistant Examiner* — Robert Eom
(74) *Attorney, Agent, or Firm* — Wenderoth Lind & Ponack, L.L.P.

(57) ABSTRACT

A peritoneal function testing apparatus tests the peritoneal function of a dialysis patient easily and with high accuracy. Standards of four kinetic parameters (CCr, Kt/V, MTACu, and MTACc) available in a definite dialysis guideline are computed in accordance with a relational expression, and a curve showing the relation between MTACu/c and the drained fluid volume is indicated in a graph together with the PET data of the patient which has been prepared separately. Thus, the peritoneal function can be evaluated based on the relative position of the patient's data and the curve showing the standard values in the graph.

8 Claims, 15 Drawing Sheets

FIG. 5

PERITONEAL FUNCTION TESTING PROTOCOL

| TIME | DIALYSIS SOLUTION | | SAMPLING | | | | REMARKS |
|---|---|---|---|---|---|---|---|
| hr | OSMOTIC PRESSURE | RETENTION PERIOD | DRAINED FLUID VOLUME | WATER REMOVAL VOLUME | BLOOD SAMPLING | URINE SAMPLING | URINE VOLUME (URINE COLLECTION) | |
| 13 | LOW | 6hr | → | → | | ↑ | | |
| 14 | | | | | | | | |
| 15 | | | | | | | | |
| 16 | | | | | | | | |
| 17 | | | | | | | | |
| 18 | | | | | | | | |
| 19 | | | D1 | VDL1 | | | | |
| 20 | LOW | 3hr | → | → | | | | |
| 21 | | | | | | | | |
| 22 | | | | | | | | |
| 23 | | | D2 | VDL2 | | | | |
| 24 | MEDIUM | 8hr | → | → | | | | NIGHTTIME |
| 1 | | | | | | | | |
| 2 | | | | | | | | |
| 3 | | | | | | | | |
| 4 | | | | | | | | |
| 5 | | | | | | | | |
| 6 | | | | | | | | |
| 7 | | | D3 | VDM1 | | | | |
| 8 | | | D4 | | | | | |
| 9 | MEDIUM | 4hr | D5 | → | | | | PET like |
| 10 | | | | | | | | |
| 11 | | | | | | | | |
| 12 | | | | | | | | |
| 13 | | | D6 | VDM2 | B1 | U1 | VU1 | |

MEASUREMENT TARGETS

| | DIALYSIS SOLUTION | BLOOD | URINE |
|---|---|---|---|
| UREA NITROGEN | ○ | ○ | ○ |
| CREATININE | ○ | ○ | ○ |

CORRELATION BETWEEN MTAC_urea AND MTAC_creatinine
FOR MEDIUM-OSMOTIC-PRESSURE DIALYSIS SOLUTION RELATIONSHIP BETWEEN PET CATEGORY AND MTACu/c RELATIONSHIP BETWEEN MTACu/c FOR
MEDIUM-OSMOTIC-PRESSURE DIALYSIS SOLUTION AND
WATER REMOVAL VOLUME AFTER 4-HOUR RETENTION RELATIONSHIP BETWEEN DRAINED FLUID VOLUME PER DAY
AND MTACu/c BASED ON CRITERIA

MASS TRANSFER MECHANISM IN PERITONEAL DIALYSIS

PERITONEAL MEMBRANE FUNCTION TEST METHOD, PERITONEAL MEMBRANE FUNCTION TEST APPARATUS AND PERITONEAL MEMBRANE FUNCTION TEST PROGRAM

BACKGROUND OF THE INVENTION

1. Technical Field

The present invention relates to a peritoneal function testing method, peritoneal function testing apparatus using a computer, and peritoneal function testing program.

1. Background Art

It is believed that there are presently about 250,000 patients with chronic renal failure in Japan. Of them, 96% to 97% receive hemodialysis as a maintenance treatment while the remaining 3% to 4% receive peritoneal dialysis.

"Dialysis" here means a process of removal of certain molecules from body fluid due to a concentration gradient by filtering it across a membrane, making use of different molecular weights. Thus, this process assists impaired renal function of the patients by dissolving various substances which are accumulated in the body through metabolic activities solutes (such as urea (U) as a uremic toxin and creatinine (Cr)), electrolytes ($Ca^{2+}$, $Cl^-$, $Na^+$, and $K^+$), excess water and the like out of the body fluid into a dialysis solution, and by then discharging the dialysis solution from the body as drained fluid. Two distinguished methods used for dialysis are hemodialysis (HD) and peritoneal dialysis (PD). Hemodialysis is a mechanical blood purification procedure to pass blood through the extracorporeal circulation, while peritoneal dialysis is a blood purification procedure achieved by infusing a dialysis solution into the peritoneal cavity and filtering blood through the peritoneum. Conventionally, either one of the dialysis procedures has been applied to the patients. In the case when deficient renal function cannot be fully compensated, it is considered as desirable to perform extracorporeal dialysis treatment using hemodialysis.

With peritoneal dialysis, the patients perform dialysis treatment mainly at home. The home dialysis involves the repetition of the following steps several times a day: introduction of a dialysis solution into the peritoneal cavity performed by patients themselves using a catheter; retention of the introduced dialysis solution for several hours; and then drainage of the dialysis solution. The patient records the amount of excess water drained from the body (referred to as the "volume of water removal") every time when a dialysis solution is drained, and submits the records to doctors in a subsequent medical examination to obtain a prescription. Such a peritoneal dialysis procedure is called CAPD (Continuous Ambulatory Peritoneal Dialysis).

Doctors generally conduct PET (Peritoneal Equilibration Test, 1987) on a patient, and selects an appropriate remedy based on the results of the test conducted on peritoneal function of the patient. PET classifies peritoneal function into four categories, High (large volume of water removal and small uremic toxin removal), High Average, Low Average, and Low (small volume of water removal and large uremic toxin removal) by plotting the following ratios against a PET curve: a ratio of the concentration of creatinine in the drained fluid and that in the body fluid (D/PCrea) and a ratio of the concentration of glucose in the drained fluid and that in the dialysis solution in the peritoneum immediately after the injection of the dialysis solution (D/DOglu). It should be noted that PET is conducted with a retention period of 4 hours and 2 L of a dialysis solution with a medium osmotic pressure (400 mOsm/kg-solvent). The PET curve was prepared using the average values and standard deviations of D/PCrea and D/DOglu calculated based on. PET results in 100 cases of Americans and Europeans. PET is a simple testing method and offers an option on a peritoneal dialysis modality based on the categories, thus is clinically useful. In Japan, 60% or more of the patients with chronic renal failure have taken PET.

In recent years, a peritoneal dialysis system that examines the state of peritoneal-function of a patient with use of a computer such as a PC has been developed (see Japanese Laid-Open Patent Application Publication No. 2000-140100). This peritoneal dialysis system can evaluate peritoneal function such as the volume of water removal, MTAC (an overall mass transfer-area coefficient), Kt/V (urea nitrogen clearance), and CCr (creatinine clearance) by computing mathematical models such as Pyle-Popovich model, which is known as a macroscopic model of peritoneal dialysis, based on patient's data such as the concentration of each solute, the volume of water removal and so on obtained by conducting PET.

Patent Document 1: Japanese Laid-Open Patent Application Publication No. 2000-140100

Patent Document 2: Japanese Laid-Open Patent Application Publication No. 2005-27886

However, a peritoneal function testing method using the above-mentioned PET has the following problems.

That is, while peritoneal function needs to be assessed with comprehensive evaluations of peritoneal function of each patient, such as the rates of solute removal and transperitoneal water removal, only parameters such as concentrations of solutes and water removal volume can be calculated from the results of PET. In other words, PET calculates respective parameters merely as discrete numerical values and does not reveal a specific correlation therebetween. This is considered to be a critical problem when, for example, judging a switching point from peritoneal dialysis to hemodialysis due to a deterioration of peritoneal function.

Also, conventionally, peritoneal function is classified into four graduated categories (High-category, High Average-category, Low average-category, and Low-category) based on the numerical range of MTAC obtained in PET to provide a judgmental basis for the above-mentioned switching point. That is, by assessing peritoneal function of a patient according to the category the patient currently belongs, a basis for a current and future dialysis planning is provided. However, although each category is conventionally considered to be in a numerical range of its own, study by the inventors of the present invention has revealed that, as shown in FIG. 10, multiple categories belong to numerical ranges which overlap with each other. This indicates that a single MTAC numerical value belongs to more than one category, suggesting that the accuracy of categorization is low. This uncertainty becomes a major issue especially when a judgment is to be made on the above-mentioned switching point, and is a problem in dialysis planning requiring an early resolution. If the switching point is misjudged, excessive strain may be placed on the peritoneum, causing a possibility for the patient to have complications with peritonitis or encapsulated peritoneal sclerosis.

The present invention was conceived in view of the above problems, and aims to provide, although relatively simple, a method for testing peritoneal function with a higher accuracy than the conventional testing methods, a peritoneal function testing apparatus and a peritoneal function testing program which use the above-mentioned method.

SUMMARY OF THE INVENTION

In order to achieve the above-mentioned aim, the present invention provides a peritoneal function testing method comprising steps of: (i) plotting MTACu/c and a drained fluid volume, which are included in results of a peritoneal function test of a patient, in a coordinate system presenting an MTACu/c-drained-fluid-volume curve as a baseline; and (ii) evaluating the results based on positions of (a) the plotted MTACu/c and drained fluid volume and (b) the curve, the MTACu/c being a ratio between MTACu, which is an overall mass transfer-area coefficient for urea nitrogen, and MTACc, which is an overall mass transfer-area coefficient for creatinine.

The present invention also provides a peritoneal function testing method comprising: a substitution step of performing, in a formula using four parameters of MTACu, MTACc, CCr, and Kt/V, a reference-value substitution for at least one of the four parameters, the MTACu being an overall mass transfer-area coefficient for urea nitrogen, the MTACc being an overall mass transfer-area coefficient for creatinine, the CCr being a clearance for creatinine, and the Kt/V being a clearance for urea; a computation step of computing the formula after the substitution step; and an evaluation step of evaluating a relationship between a peritoneal permeability and a drained fluid volume based on results of a peritoneal function test by comparing computation results obtained in the computation step with MTACu/c and the drained fluid volume included in the results of the peritoneal function test.

Here, the above-mentioned formula is a formula based on kinetics of a peritoneal dialysis method.

Also, in the substitution step, (i) the reference-value substitution can be performed for the CCr and the Kt/V, and (ii) the formula can include the MTACu/c as a term therein, which is a ratio between the MTACu and the MTACc.

Additionally, in the substitution step, the formula can be a formula (7), $$Kt = V_D \left\{ 1 - \left(1 - \frac{CCr}{V_D}\right)^{MTACu/c} \right\} \quad (7)$$

or a modified formula of the formula (7), where $V_D$ is a drained fluid volume for a solution with a medium osmotic pressure after a predetermined retention period.

On the other hand, in the substitution step, the formula can be a formula (8), $$Kt = V_D \left\{ 1 - \left\{\frac{V_D}{V_D(0)}\right\}^{-n} \left\{\left\{\frac{V_D}{V_D(0)}\right\}^{n}\left(1 - \frac{CCr}{V_D}\right)\right\}^{MTACu/c} \right\} \quad (8)$$

or a modified formula of the formula (8), where n is 0.5 or 1, $V_D$ is a drained fluid volume for a solution with a medium osmotic pressure after a predetermined retention period, and $V_D(0)$ is an injected fluid volume.

In addition, in the evaluation step, the computation results and the results of the peritoneal function test can be plotted in a coordinate system with the MTACu/c and the drained fluid volume as each axis, and a deterioration of peritoneal function based on the results of the peritoneal function test can be predicted in accordance with positions of the plotted results of the peritoneal function test and information obtained from the computation results.

Further in the evaluation step, when the results of the peritoneal function test are in such a numerical range that the MTACu/c is 1.44 or lower, a switching point from peritoneal dialysis to hemodialysis or from peritoneal dialysis to a combination of the peritoneal dialysis and the hemodialysis can be evaluated by taking into account a scope of the drained fluid volume in the numerical range.

The present invention also provides a peritoneal function testing apparatus (i) performing, in a formula using four parameters of MTACu, MTACc, CCr, and Kt/V, a reference-value substitution for at least one of the four parameters, the MTACu being an overall mass transfer-area coefficient for urea nitrogen, the MTACc being an overall mass transfer-area coefficient for creatinine, the CCr being a clearance for creatinine, and the Kt/V being a clearance for urea; (ii) computing the formula after the substitution step; and (iii) evaluating a relationship between a peritoneal permeability and the drained fluid volume based on results of a peritoneal function test by comparing computation results obtained in the computation step with MTACu/c and the drained fluid volume included in the results of the peritoneal function test.

The present invention further provides a peritoneal function testing program causing a computer to execute: a substitution step of performing, in a formula using four parameters of MTACu, MTACc, CCr, and Kt/V, a reference-value substitution for at least one of the four parameters, the MTACu being an overall mass transfer-area coefficient for urea nitrogen, the MTACc being an overall mass transfer-area coefficient for creatinine, the CCr being a clearance for creatinine, and the Kt/V being a clearance for urea; a computation step of computing the formula after the substitution step; and an evaluation step of evaluating a relationship between a peritoneal permeability and the drained fluid volume based on results of a peritoneal function test by comparing computation results obtained in the computation step with MTACu/c and the drained fluid volume included in the results of the peritoneal function test.

As described above, the present invention enables an evaluation of peritoneal function in accordance with continuous and time-course numerical changes of $MTAC_u/_c$ and the drained fluid volume. This is made possible by obtaining a referential correlation curve of the drained fluid volume and $MTAC_u/_c$ based on the formulae of the four parameters used in the kinetics of the conventional peritoneal dialysis method and comparing the correlation curve and the testing results.

In other words, conventionally, peritoneal function is evaluated by simply performing a categorization based on the numerical values of MTAC measured in PET. On the other hand, the present invention uses the above-mentioned correlation curve derived from the formulae based on the kinetics so as to continuously examine a scope of $MTAC_u/_c$. As a result, an accurate prediction may be made on a judgment on the switching point from PD to HD, providing an advantage of enabling an appropriate dialysis planning. Consequently, compared to the conventional evaluating method, which is confined to a straightforward evaluation based on the numerical values of MTAC obtained from PET, the present invention can recognize dynamic alterations of the two peritoneal function parameters, $MTAC_u/_c$ and the drained fluid volume, thereby allowing a more detailed and accurate examination of the dialysis modality.

In this way, a risk of patient's having complications with peritonitis or encapsulated peritoneal sclerosis (EPS) caused by a strain on the peritoneum due to a misjudgment of the switching point can be avoided.

It should be noted that conventionally, there is also a system which predicts dynamic alterations of numerical values of MTAC based on the numerical values of MTAC obtained in PET. However, this system requires correspondingly complex computations and special processing. On the other hand, the present invention obtains the formulae used in the computation of the four parameters from the conventional derivation formulae of MTAC, thereby allowing relatively easy computation in implementation.

BRIEF DESCRIPTION OF THE DRAWINGS

FIG. 5 shows an example of a peritoneal function testing protocol;

DESCRIPTION OF REFERENCE NUMERALS

Figure 1:
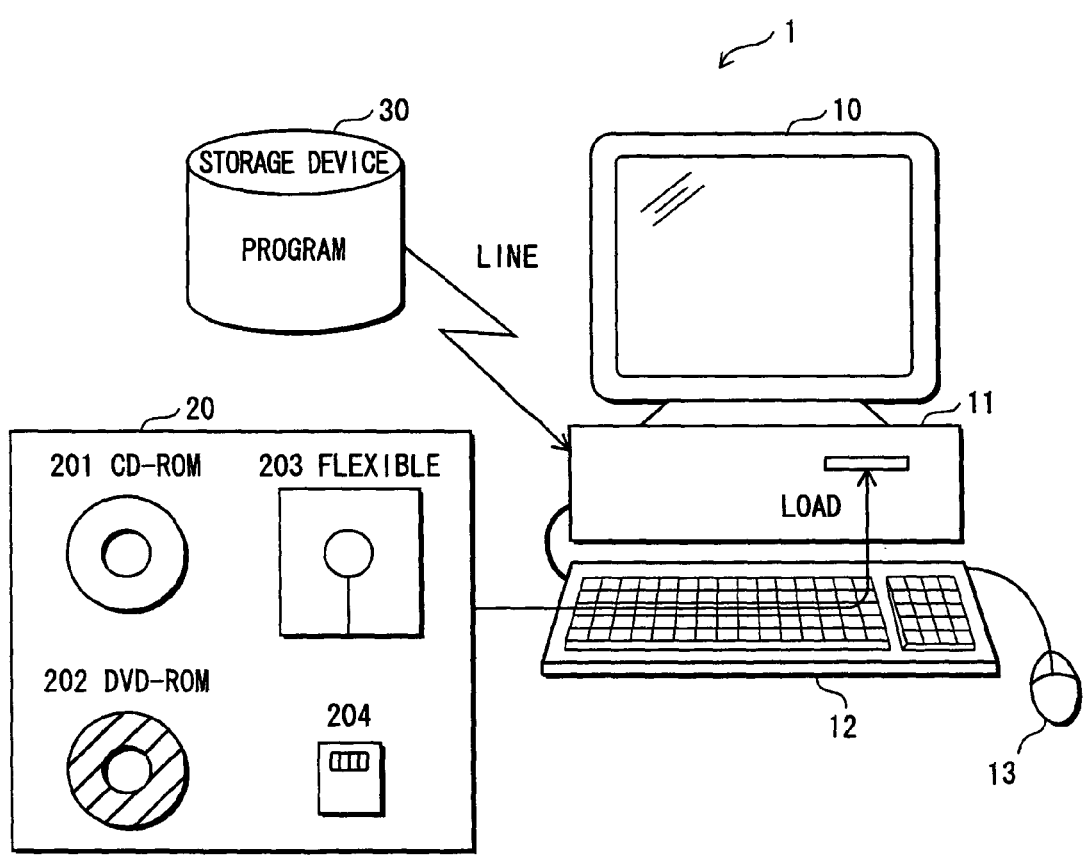
FIG. 1 is a schematic view of a first embodiment, a peritoneal function testing apparatus using a PC.

1 . . . peritoneal function testing apparatus using a PC
10 . . . monitor.
11 . . . PC
12 . . . keyboard
20 . . . recording media
30 . . . storage device via a communication line
40 . . . input unit
50 . . . storage unit
60 . . . computation unit
70 . . . output unit
401 . . . reference value input subunit
402 . . . patient-data input subunit
501 . . . $MTAC_u/_c$-drained-fluid-volume curve storage subunit
502 . . . patient-data storage subunit
701 . . . $MTAC_u/_c$-drained-fluid-volume curve output subunit
702 . . . patient-data output subunit

DETAILED DESCRIPTION OF THE INVENTION

<First Embodiment>
1. Configuration of Peritoneal Function Testing Apparatus

First, a configuration of a peritoneal function testing apparatus of a first embodiment of the present invention will be described. The peritoneal function testing apparatus is also used as a dialysis planning apparatus and includes a program (peritoneal function testing program), installed in a general-purpose computer, for performing a peritoneal dialysis testing method.

FIG. 1 shows an exemplary configuration of a peritoneal function testing apparatus in accordance with the present invention. The peritoneal function testing apparatus is shown as a personal computer (PC) 1 comprising: a main body 11, a keyboard 12 and a mouse 13 as input means connected to the main body 11, and a monitor 10 as a data output unit (display unit). The main body 11 includes a publicly known CPU, a hard disk drive (HDD), a memory, and the like therein. The peritoneal function testing program of the present invention may be read into the PC 1 with use of, for example, various transportable recording media 20 (a CD-ROM 201, a DVD-ROM 202, a flexible disc 203, a memory card 204, etc.). Alternatively, the program can be read into the PC 1 from a storage device 30 such as a different server, PC or the like via a communication line, as shown in FIG. 1. Once being read, the peritoneal function testing program is configured to be stored in the HDD of the PC 1, along with patient's data.

Figure 2:
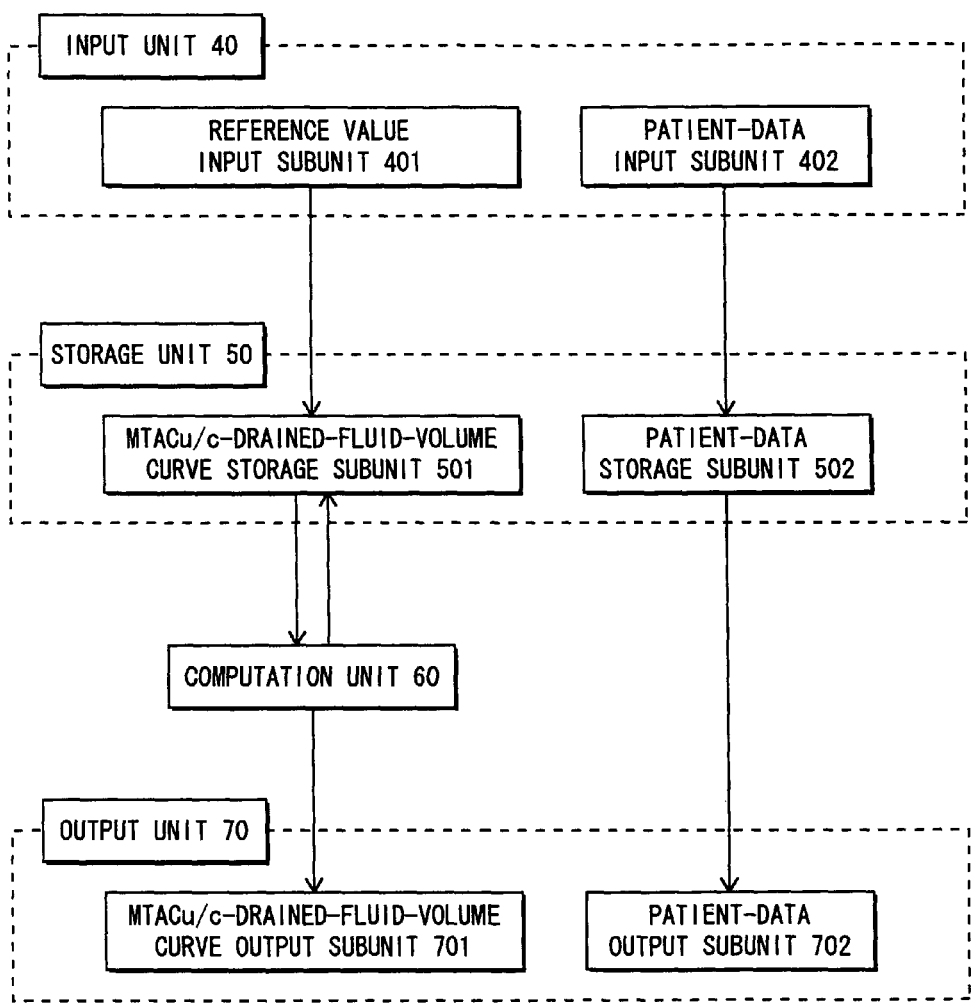
FIG. 2 is a function block diagram schematically showing a configuration of the peritoneal function testing apparatus.

Next, the configuration of the peritoneal function testing apparatus is described by dividing it into functional blocks based on functions of the peritoneal function testing program. As shown in FIG. 2, the peritoneal function testing apparatus is divided into an input unit 40, a storage unit 50, a computation unit 60, and an output unit 70.

The input unit 40 (keyboard 12 and mouse 13) also includes a reference value input subunit 401 and a patient-data input subunit 402 related to PET testing results. Of these, the reference value input subunit 401 provides an input means for inputting reference values of four kinetics parameters used in computation of a formula (7), which will be described later.

The storage unit 50 (HDD) includes a storage subunit 502 and a $MTAC_u/_c$-drained-fluid-volume curve storage subunit 501. The storage subunit 502 stores patient's data input through the input unit 40; the $MTAC_u/_c$-drained-fluid-volume curve storage subunit 501 stores results of computation executed by the computation unit 60 based on the numerical values inputted through the reference value input unit 401.

The computation unit 60 (CPU) mainly executes computations based on the above-mentioned program and manages respective data stored in the storage unit 50.

The output unit 70 (monitor 10) includes a $MTAC_u/_c$-drained-fluid-volume curve output unit 701 and a patient-data storage unit 702. The $MTAC_u/_c$-drained-fluid-volume curve output unit 701 displays a $MTAC_u/_c$-drained-fluid-volume curve which is the result of computations performed by the computation unit 60; the patient-data storage unit 702 displays the data in the patient data storage unit 502.

The peritoneal function testing apparatus made up of the above functional blocks performs computation of the formula (the formula (7) which will be described later) including the four kinetics parameters (CCr, Kt/V, $MTAC_u$, $MTAC_c$) by substituting a reference values for CCr and Kt/V, respectively, in accordance with the predetermined dialysis guideline selected by the operator. After that, the peritoneal function testing apparatus displays, on the monitor, a graph curve showing a relationship between $MTAC_u/_c$ and the drained fluid volume obtained from the above computation results. Along with the above graph curve, separately prepared PET data of the patient is displayed on the monitor, enabling an evaluation of peritoneal function based on relative positions, in the graph, of the patient's data and the curve in accordance with the reference values.

Such an evaluation method using a curve indicating the relationship between $MTAC_u/_c$ and the drained fluid volume has been made available for the first time by the inventors of the present invention. This method enables an evaluation of status of peritoneal function over time (a mechanism of deterioration in peritoneal function) with a higher accuracy compared to the testing method based on the conventional PET testing results.

The following describes the operation of this program in detail.

1-2. About Peritoneal Function Testing Program

Figure 3:
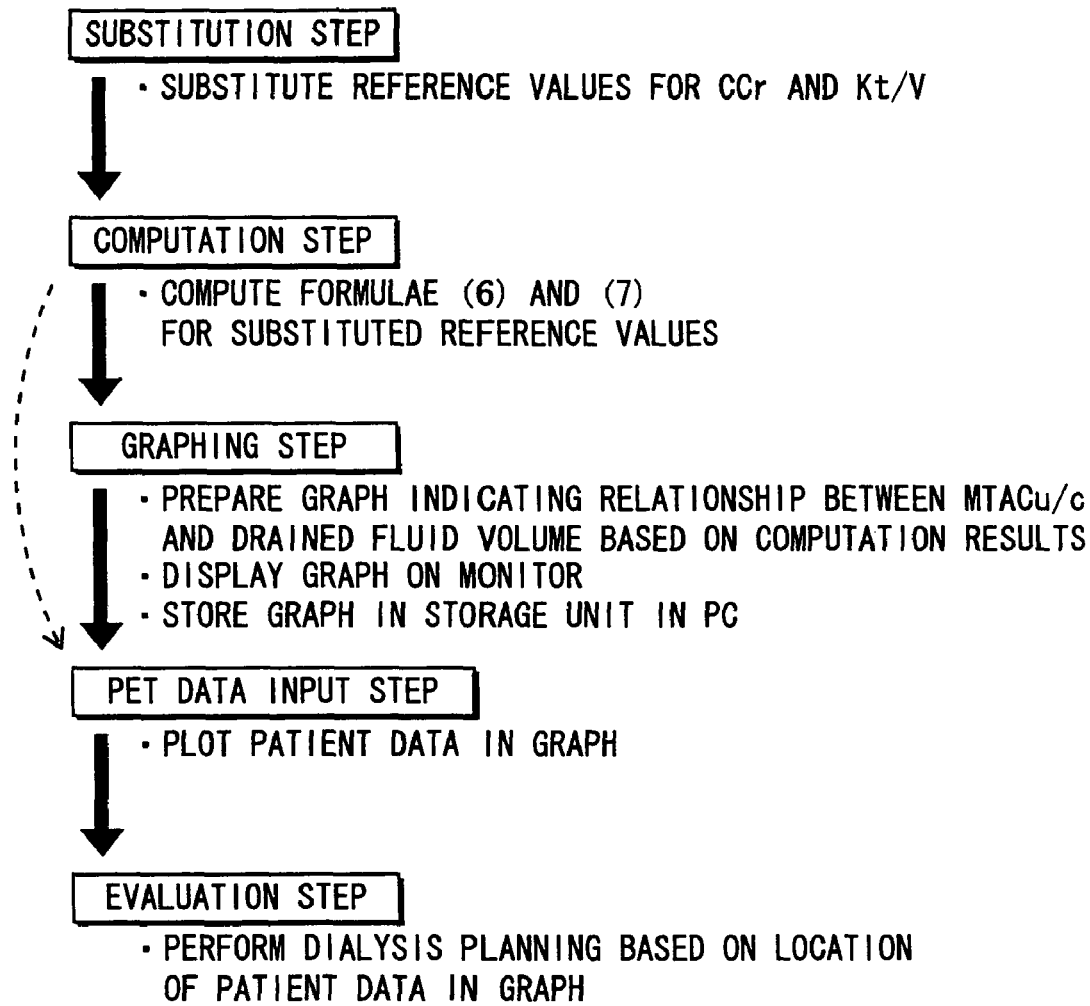
FIG. 3 shows a process flow of a peritoneal function testing program.
Figure 4:
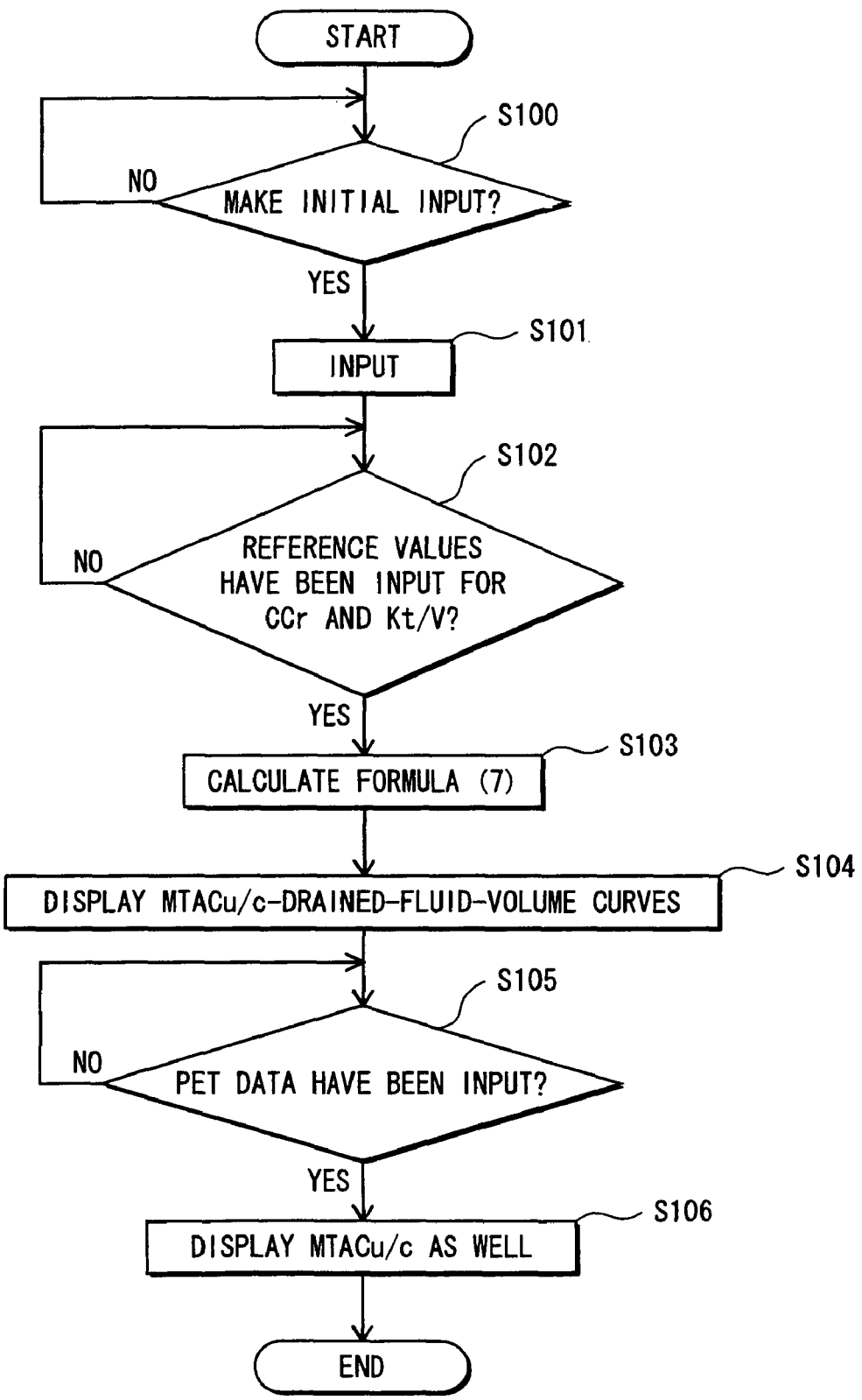
FIG. 4 is a flowchart of the peritoneal function testing program.

FIG. 3 shows an overall process flow of the peritoneal function testing program implemented in the PC 1. FIG. 4 shows a flow chart of the present program.

As shown in FIG. 3, when using the apparatus, the operator first activates the peritoneal function testing program installed on the PC 1 and performs an initial input of a reference value, in accordance with a dialysis guideline, for CCr and Kt/V among four parameters (CCr, Kt/V, $MTAC_u$, $MTAC_c$) related to peritoneal function. These four parameters are required for computations in the peritoneal function testing (a substitution step in FIG. 3, S100 and S101 in FIG. 4). Here, as the reference value, it is preferable to use an average value according to a guideline which has a sufficiently large number of population parameters and thus is reliable, such as clinical data of National Kidney Foundation (NKF-DOQI). Here, CCr=60.0 L/week/1.73 m$^2$; Kt/V=2.00 will be used as fixed values for substitution (S102 in FIG. 4).

Figure 6:
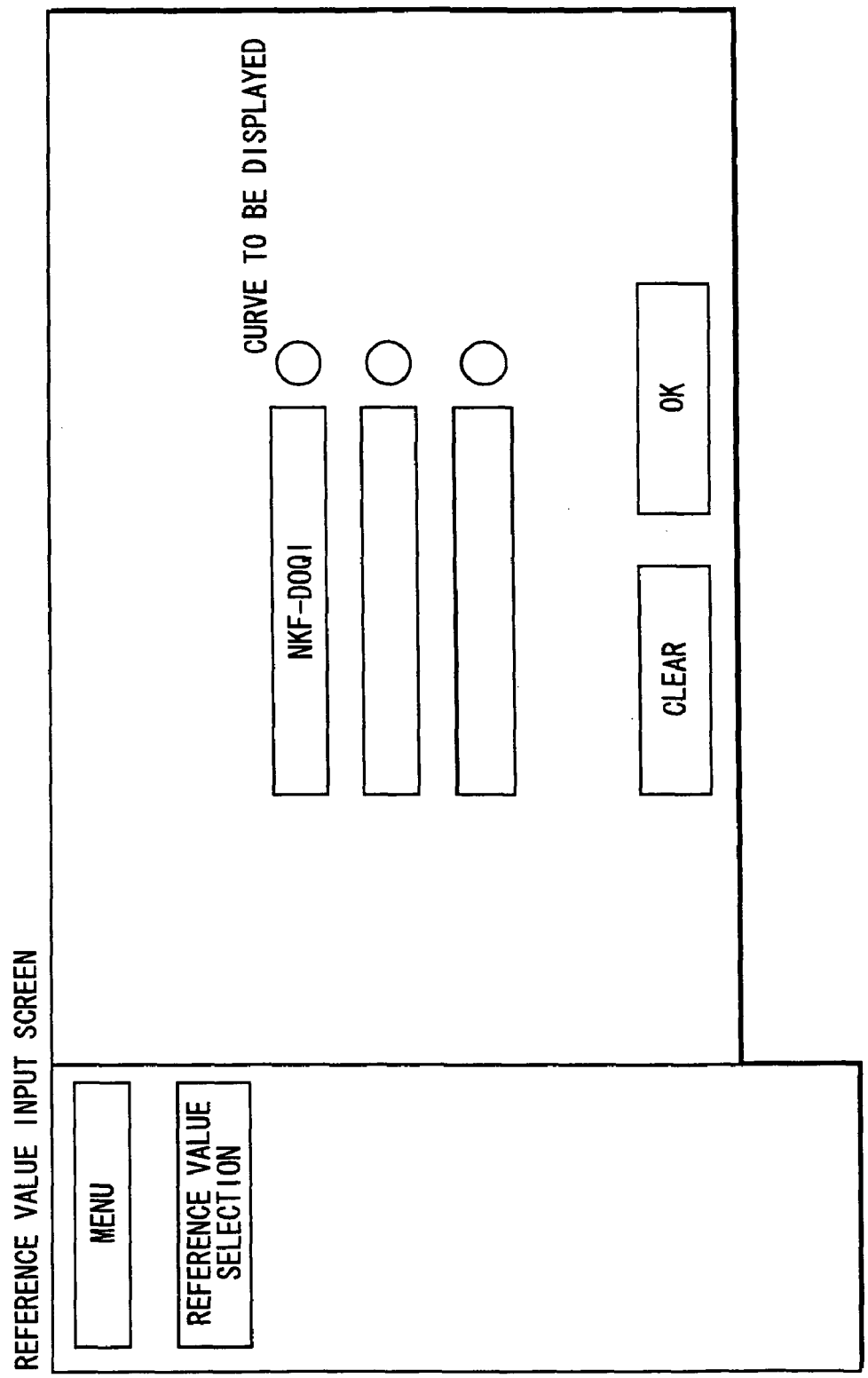
FIG. 6 is an input screen for reference values of a dialysis guideline.

As to an input method of the reference values based on the dialysis guideline, for instance, an input can be performed by inputting after pressing the <initial input> button in the input screen in FIG. 6. Subsequently, the program becomes executable, and the PC 1 performs computation, under the direction of the operator, in accordance with the following equation (7) which includes the above-mentioned four parameters (computation step, S103 in FIG. 4). Here, the fixed values are substituted into the reference values CCr and Kt/V in the formula (7), thus the actual calculation will be performed on a formula which has two variables in $V_D$ and $MTAC_u/_c$.

$$Kt = V_D \left\{ 1 - \left( 1 - \frac{CCr}{V_D} \right)^{MTACu/c} \right\} \quad (7)$$

Here, t is a retention period, and $V_D$ is a drained fluid volume after a dialysis solution with a medium osmotic pressure is retained for a predetermined period of time (here, 4 hours).

Next, the PC 1 presents, on the monitor 10, a graph showing a curve ($MTAC_u/_c$-drained-fluid-volume curve) indicating a relationship between the drained fluid volume and a MTAC ratio of urea nitrogen and creatinine ($MTAC_u/_c$) which have been obtained from the results of the previous computation step (graphing step, S103 in FIG. 4). At the same time, the PC 1 stores the computation results relating to the curve into the $MTAC_u/_c$-drained-fluid-volume curve storage subunit 501.

Here, it should be noted that from the second activation of the apparatus, that is, after the computation results obtained by S103 are stored in the above-mentioned storage subunit 501, the program steps need to be executed only from S104 to S106. In other words, the curve which has been stored in the above-mentioned storage subunit 501 can be presented as a graph (S104) simply by pressing a radio button to select the predetermined curve after displaying the screen in FIG. 6 following the program activation.

Following that, the operator conducts a test such as PET or the like on a particular patient to prepare a dialysis planning by the present apparatus. FIG. 5 shows data acquisition steps when PET is conducted.

In the data acquisition steps, 2 L volume of a dialysis solution with a medium osmotic pressure of 400 (mOsm/kg-solvent) is used, and the dialysis solution of the patient is exchanged 4 times in total, starting from the previous day, at intervals varying approximately from 3 to 8 hours. During these steps, a blood sample is taken on a regular schedule, and a urine sample is collected while the concentration of each solute is checked. The osmotic pressure of the dialysis solutions and the number of exchanges can take values other than the above.

The items of clinical data obtained here include the amount of collected urine and the concentration of each solute in urine (urinary urea nitrogen, urinary creatinine, urinary protein, and urinary sodium). The items also include concentrations of blood-total protein, albumin, serum creatinine, urea nitrogen, glucose, sodium, chloride and so on, obtained from the blood samples. Here, naturally, pre-measured data can be used for PET.

Figure 7:
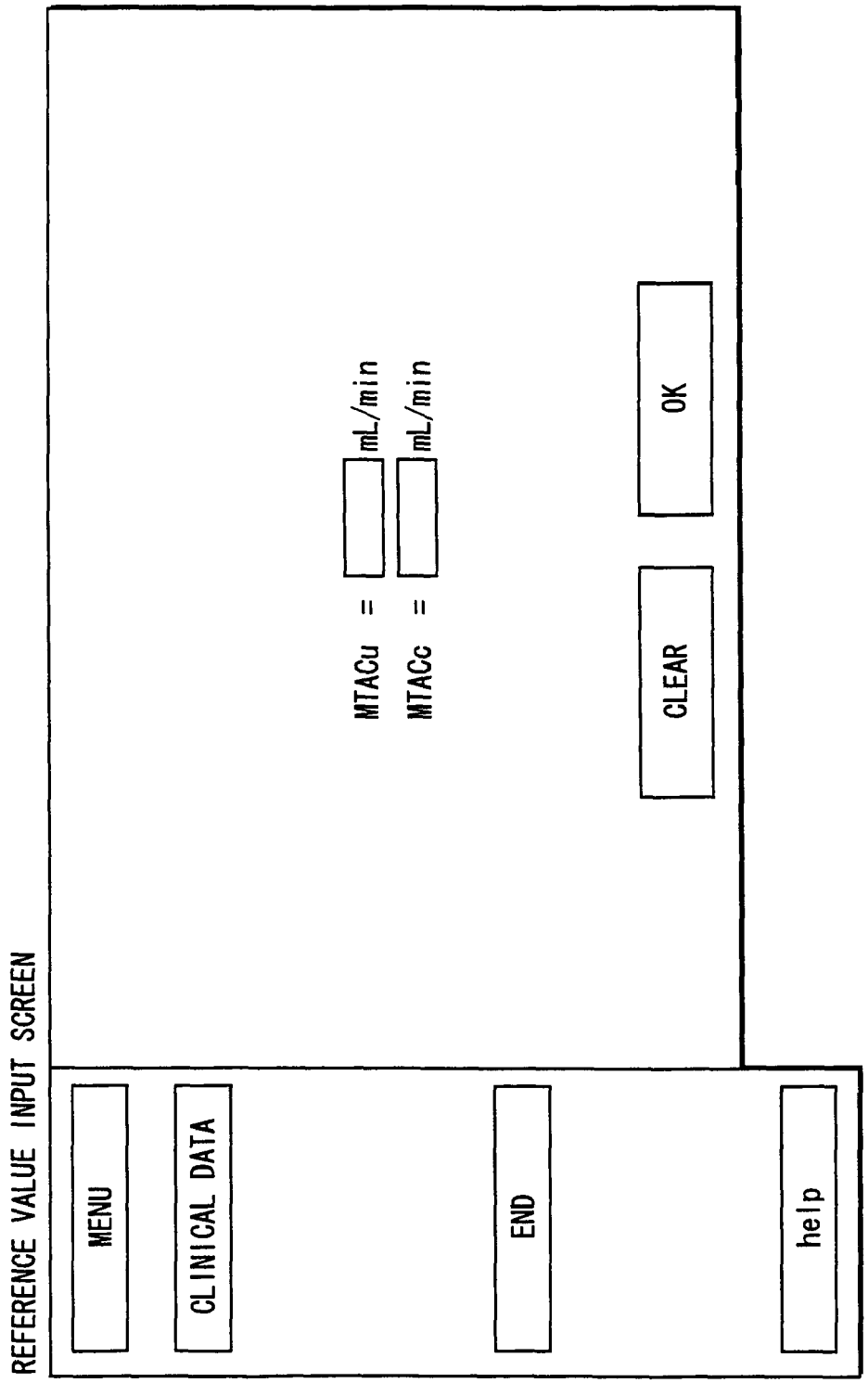
FIG. 7 is an input screen for results of PET.

Following the above, as shown in FIG. 7, the operator inputs the results of PET ($MTAC_u$ and $MTAC_c$) into the PC 1 using the input screen presented on the monitor (PET data input step, S105 in FIG. 4).

Figure 8:
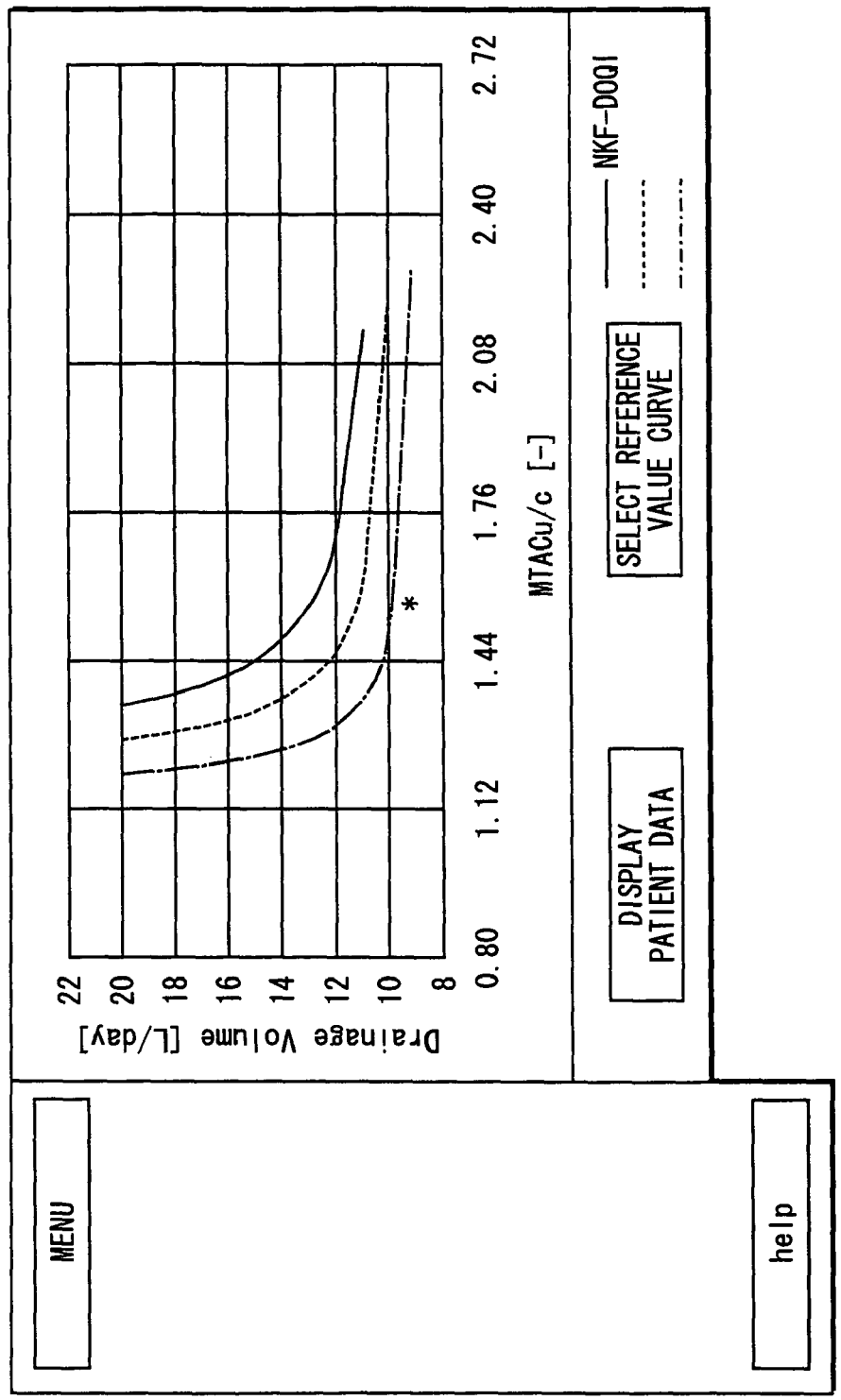
FIG. 8 shows a graph display of $MTAC_u/_c$-drained-fluid-volume curve and patient's data.

After the operator presses the <OK> button presented on the display on the completion of the input, the PC 1 presents the patient's data by plotting it in the graph, along with the $MTAC_u$-drained-fluid-volume curve (FIG. 8, S104 in FIG. 4). Consequently, the operator can examine the peritoneal function based on the relative positions of the plotted data of the PET results and the above-mentioned curve (evaluation step in FIG. 3). Enabling a peritoneal function test by using such a graph is a major feature of the present invention.

The following describes an exemplary case of a dialysis planning using the apparatus, conducted on a patient X who is on a peritoneal dialysis treatment.

According to the data on the patient X obtained from PET, $MTAC_u/_c$ was 1.66, and the total volume of the drained fluid was 10 L. The operator selects a reference value in accordance with one guideline among predetermined guidelines, a NKF-DOQI guideline, a CANUSA Study guideline, and a DOQI guideline, presented on the screen shown in FIG. 6 (here, the NKF-DOQI guideline is selected, and values CCr=60.0 L/week/1.73 m$^2$ and Kt/V=2.00 are each substituted as the reference values) and plots the $MTAC_u/_c$ value of the patient X in the graph through the screen shown in FIG. 7 (* in FIG. 8). While reference values are not limited to those of the above-mentioned guidelines, NKF-DPQI guideline can be used as a sufficiently reliable source of the reference values. Also, if the strictest guideline among existing major guidelines is adopted, excess strain on the peritoneum due to the peritoneal dialysis can be prevented.

Consequently, as shown in FIG. 8, the graph display of the $MTAC_u$-drained-fluid-volume curve with a plot of the data of the patient X is obtained.

According to this figure, based on the NKF-DOQI guideline, the ideal volume of the drained fluid when $MTAC_u/_c$ is 1.66 is approximately 13 L. However, as to the patient X, only 10 L of drained fluid is obtained, thereby indicating that the drained fluid volume is insufficient based on this guideline. Accordingly, it can be said that the intensity of the dialysis in the current peritoneal dialysis plan is insufficient, requiring a consideration on an increase of the number of the peritoneal dialysis or a switch to a hybrid remedy including both peritoneal dialysis and hemodialysis for the future treatment.

Additionally, while $MTAC_u/_c$ of the patient X is 1.66, this figure will be lower if the peritoneal function deteriorates. The curve in the graph indicates a rapid change in slope, which starts at around 1.44, a value not far away from 1.66, implying that the ideal volume of drained fluid is going to increase rapidly. Therefore, considering the current status of the peritoneal function of the patient X, it is difficult to presume that a sufficient volume of drained fluid can be ensured by peritoneal dialysis, and now it has come to a stage to consider relying on the hemodialysis. This $MTAC_{u/c}$ value "1.44" is a turning point of the curve, substantially throughout the reference values of respective guidelines, offering a useful basis for judging the switching point.

It should be noted that FIG. 8 shows curves other than the NKF-DOQI guideline, and if based on these curves, the ideal volume of drained fluid for a $MTAC_{u/c}$ can be less compared to when based on the NKF-DOQI guideline. Accordingly, based on the judgment of the operator, a doctor, flexibility of the dialysis planning is ensured in accordance with the guideline in use, thereby allowing a sensitive peritoneal function test conducted by each doctor (operator).

Also, according to the present invention as above, it is possible to appropriately predict the switching point from peritoneal dialysis to hemodialysis by recognizing the relative positions of the above-mentioned curve and the patient's data, and the change in slope of the above-mentioned curve. Therefore, the present invention can be expected to be highly effective, for example, in preventing patients from having complications with peritonitis which may occur due to excessively intense peritoneal dialysis. Consequently, life extension treatment can be conducted on the patient based on an appropriate dialysis planning.

Based on the above-mentioned conventional, comparatively less accurate PET categorizing method, it is considerably difficult to make a judgment on such a time-course dialysis planning. The present invention, however, enables such planning by studying the relative positions of the $MTAC_u$-drained-fluid-volume curve and the data of the patient, as well as the slope of the curve.

In addition, while the peritoneal function testing apparatus is mainly characterized by computation based on the formula (7) and the content of the graph display thereof, materials such as a separate special apparatus, a calculation method, and new data which has not been used before, are not required to realize its function. Therefore, characteristically, the function of the present apparatus can be realized easily, at a low cost, based on the conventional PET data.

1-3. About How to Derive Formula (7) from Existing Formula

Next, described below is a derivation method of the formula (7) computed by the above-mentioned program. Since the formula (7) used in the present invention is derived from an existing MTAC derivation formula it is relatively simple and easy to use.

Figure 15:
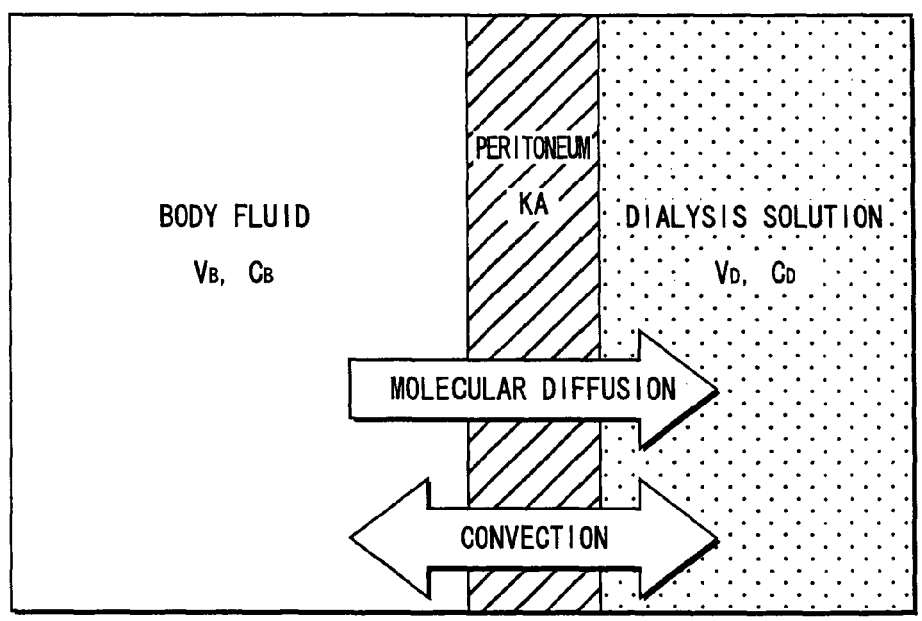
FIG. 15 is a schematic diagram of a mass transfer mechanism in peritoneal dialysis.

FIG. 15 shows a model used to explain a general peritoneal dialysis function. At and around the peritoneum, molecular diffusion and convection of solutes such as urea nitrogen, creatinine, etc. take place between body fluid such as blood, lymphatic fluid and the like and dialysis solution via the peritoneum. Here, the parameter used to represent the peritoneal function is KA (MTAC; overall mass transfer-area coefficients) or Kt/V. In consideration of the model here, a simplified computation formula for MTAC can be obtained as shown as the formula (1). Note that this simplified computation formula itself is publicly known.

$$MTAC = -\frac{V_D}{t} \ln \left| \left\{ \frac{V_D}{V_D(0)} \right\}^n \frac{C_D - C_B}{C_D(0) - C_B} \right| \quad (1)$$

where t: retention period;

$V_D(0)$: volume of injected fluid;

$V_D$: volume of the drained fluid after the dialysis solution with a medium osmotic pressure is retained for 4 hours;

$C_D(0)$: concentration of a solute in the dialysis solution in the peritoneum immediately after injecting the dialysis solution with the medium osmotic pressure;

$C_D$: concentration of a solute in the drained fluid after the dialysis solution with the medium osmotic pressure is retained for 4 hours; and $C_B$: concentration of a solute in the body fluid.

It should be noted that in the formula (1), if n=0, it is Henderson's formula; if n=0.5, it is Yamashita's formula; and if n=1.0, it is Babb-Garred's formula. In the present invention, the n can adopt any one of the three numerical values. In the first embodiment, the formula (7) is derived with n=0.

Hence, here, a description will be given on a case where n=0 (when Henderson's formula is adopted).

It is necessary to determine a correlation between the MTAC ratio of the urea nitrogen and creatinine ($MTAC_{u/c}$) calculated by the formula (1) and the drained fluid volume of the dialysis solution with the medium osmotic pressure, which has been retained for 4 hours. As to the drained fluid volume, an average value of drained fluid volume of PET in PD NAVI test and the drained fluid volume of the dialysis solution with the medium osmotic pressure after 4 to 5 hour retention can be used. Computation is conducted by calculating creatinine clearance (CCr) and urea nitrogen clearance (Kt)

The formula (1) is expanded as follows.

$$\frac{C_D}{C_B} = 1 + \frac{C_D(0) - C_B}{C_B} \left\{ \frac{V_D}{V_D(0)} \right\}^{-n} \exp\left(-\frac{MTAC}{V_D} t\right) \quad (1')$$

Here, if $C_B$ is sufficiently larger than $C_D(0)$, the formula will be as follows.

$$\frac{C_D}{C_B} = 1 - \left\{ \frac{V_D}{V_D(0)} \right\}^{-n} \exp\left(-\frac{MTAC}{V_D} t\right) \quad (1'')$$

Here, if the formula (1") is used, the clearance for the 4-hour retention is as follows.

(2)

$$\frac{V_D C_D}{C_B} = V_D \left\{ 1 - \left\{ \frac{V_D}{V_D(0)} \right\}^{-n} \exp\left(-\frac{MTAC}{V_D} t\right) \right\} \quad (2)$$

The clearance can be calculated from the drained fluid volume, the retention time, and MTAC. If the formula (2) is described using CCr and Kt and rearranged, they will be expressed as follows.

$$MTAC_{crea} = -\frac{V_D}{t} \ln\left\{ \left\{ \frac{V_D}{V_D(0)} \right\}^n \left\{ 1 - \frac{CCr}{V_D} \right\} \right\} \text{ for creatinine} \quad (3)$$

$$MTAC_{urea} = -\frac{V_D}{t} \ln\left\{ \left\{ \frac{V_D}{V_D(0)} \right\}^n \left\{ 1 - \frac{Kt}{V_D} \right\} \right\} \text{ for urea nitrogen} \quad (4)$$

The ratio between the formulae (3) and (4) is expressed as follows.

$$MTACu/c = \frac{MTAC_{urea}}{MTAC_{crea}} = \frac{\ln\left\{\left\{\frac{V_D}{V_D(0)}\right\}^n\left\{1-\frac{Kt}{V_D}\right\}\right\}}{\ln\left\{\left\{\frac{V_D}{V_D(0)}\right\}^n\left\{1-\frac{CCr}{V_D}\right\}\right\}} \quad (5)$$

And, $MTAC_u/_c$ is derived from the drained fluid volume and dialysis clearance. The formula (5) is rearranged as follows.

$$\ln\left\{\left\{\frac{V_D}{V_D(0)}\right\}^n\left\{1-\frac{Kt}{V_D}\right\}\right\} = MTACu \Big/ c\left(\ln\left\{\left\{\frac{V_D}{V_D(0)}\right\}^n\left\{1-\frac{CCr}{V_D}\right\}\right\}\right) \quad (6)$$

And this can be further rearranged as follows.

$$Kt = V_D\left\{1-\left\{\frac{V_D}{V_D(0)}\right\}^{-n}\left\{\left\{\frac{V_D}{V_D(0)}\right\}^n\left(1-\frac{CCr}{V_D}\right)\right\}^{MTACu/c}\right\} \quad (8)$$

Here, in the above formula (8), assuming that n=0, the formula (7) can be derived. By modifying the formula for VD and substituting reference values into CCr and Kt/V, respectively, the $MTAC_u/_c$-drained-fluid-volume curve in FIG. 14 can be obtained.

In the present invention, n=0, and the peritoneal function testing program is operated, based on the predetermined reference values inputted by the operator through the PC 1, to compute the above formulae (6) and (7), and to obtain the $MTAC_u$-drained-fluid-volume curve ultimately.

On the other hand, in the above formula (7), n can be set to 0.5 or 1.0, alternatively. In these cases also, the $MTAC_u$-drained-fluid-volume curve can be obtained ultimately. And, with use of the formulae (6) and (7), the relationship between peritoneal function, required effectiveness of dialysis, and drained-fluid-volume can be examined, making the similar effects to the present invention obtainable.

1-4. About Comparative Test

Next, in order to evaluate the peritoneal testing method of the present invention, a comparison was made between the conventional testing method (evaluation method using PET data) and the testing method in accordance with the present invention.

[About Conventional Evaluation Method]

PET was conducted on 100 cases of patients on peritoneal dialysis treatment who are regularly treated with CAPD, CCPD (Continuous Cycling Peritoneal Dialysis), or NIPD (Nightly Intermittent Peritoneal Dialysis). Table 1 shows the average values of the clinical data. Total body fluid volume and body surface area were approximately the same as the average values of Ota, et. al (Kazuo Ota, Mitsuru Ishizaki, Tutomu Sanaka, Hidemune Naito, et al., (1999). CAPD Kanja no Rinsho Kensa-chi Chousa Houkoku. Fukumaku-Touseki '99 (Clinical Test Value Research Report on CAPD Patients: Peritoneal Dialysis '99). Kazuo Ota (ed.) pp. 383-391. Tokyo: Tokyo Igakusha).

TABLE 1

Average Values of Clinical Data of 100 Cases of Japanese Patients (Male: 76 cases, Female: 24 cases)

| | |
|---|---|
| CCr: | 57.0 L/week/1.73 m² |
| Kt/V: | 1.86 |
| Kt: | 68.8 L/week/1.73 m² |
| $MTAC_u/_c$: | 1.76 ± 0.32 |

Figure 9:
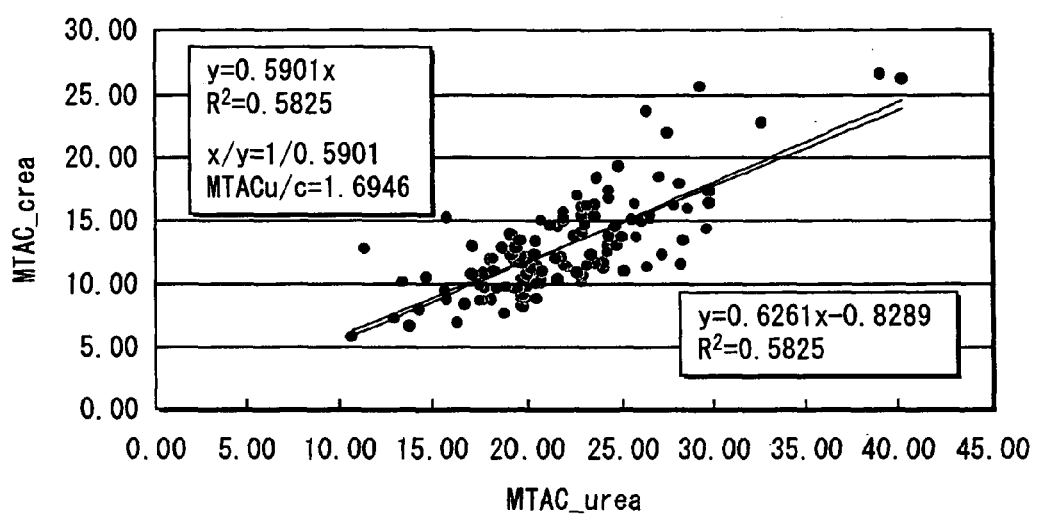
FIG. 9 shows a correlation between MTAC of urea nitrogen and creatinine for a dialysis solution with a medium osmotic pressure.

Total body fluid volume: 37 L
Body surface area: 1.73 m²
Drained fluid volume: 1033 mL/day In the following, correlations in all cases between MTAC of urea nitrogen and MTAC of creatinine are shown in FIG. 9. As shown in the figure, MTACs of small molecules (urea and creatinine) indicated a favorable correlation ($r^2 > 0.58$). Since a diffusion coefficient of a solute is proportional to negative one-half power of a molecular weight, it can be observed that the correlation between urea and creatinine, which are of small molecules, are approximate linearization. This denotes that while a numerical value of each MTAC of an individual patient may vary, the $MTAC_u/_c$ value of each patient can be considered to be constant.

Figure 10:
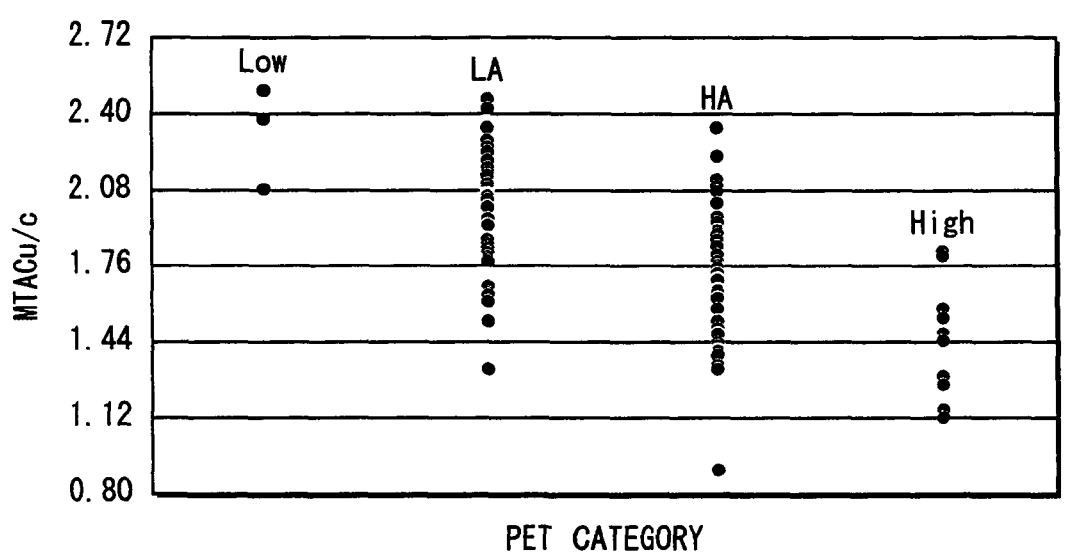
FIG. 10 shows a correlation between PET categories and $MTAC_u/_c$.

Next, relationships between $MTAC_u/_c$ and PET categories in all cases are shown in FIG. 10, and an average value of $MTAC_u/_c$ in each PET category is shown in Table 2.

TABLE 2

$MTAC_u/_c$ in each PET category (average value ± standard deviation)

| Category | $MTAC_u/_c$ | Cases |
|---|---|---|
| Low | 2.32 ± 0.21 | 3 |
| Low Average | 1.97 ± 0.25 | 36 |
| High Average | 1.69 ± 0.26 | 43 |
| High | 1.44 ± 0.20 | 18 |

Test for the Average Values (unilateral)
Low vs Low Average p < 0.058
Low Average vs High Average p < 4.05E−07
High Average vs High p < 1.86E−05

Since MTAC increases as peritoneal function deteriorates, $MTAC_u/_c$ decreases as peritoneal function deteriorates. Here, according to the conventional common evaluation method, a varying range of $MTAC_u/_c$ in each category (High category, HighAverage category, HighAverage category, and Low Average category) is independently recognized from each other in a coordinate system presenting the relationship between the Dialysate/Plasma ratio (D/P) and the retention period (so-called "D/P curve"). According to the inventors of the present invention, however, these categories in fact are found to overlap with each other, as shown in FIG. 10. Accordingly, when based on a range of numerical value of $MTAC_u/_c$ which exists in a vicinity of a border of a category range, it is difficult to properly perform PET categorization based on the numerical value, thus it is not possible to perform a peritoneal function test with high accuracy. Additionally, if the categorization is not conducted properly, the intensity of peritoneal dialysis may not be set properly.

Next, a relationship among CCr, Kt/V, drained fluid volume, and $MTAC_u/_c$ was studied using the average values in the Table 1 in the formulae (6) and (7). FIGS. 12A to 12C and FIGS. 13A and 13B show the relationship between CCr and Kt/V under the assumption that a daily drained fluid volume=10.0, 11.0, 12.0, 13.0, and 14.0 L, and $MTAC_u/_c$=1.12, 1.44, 1.76, 2.08, 2.40, and 2.72, respectively. In the figures, "KA" and "MTAC" are synonymous.

Figure 12A:
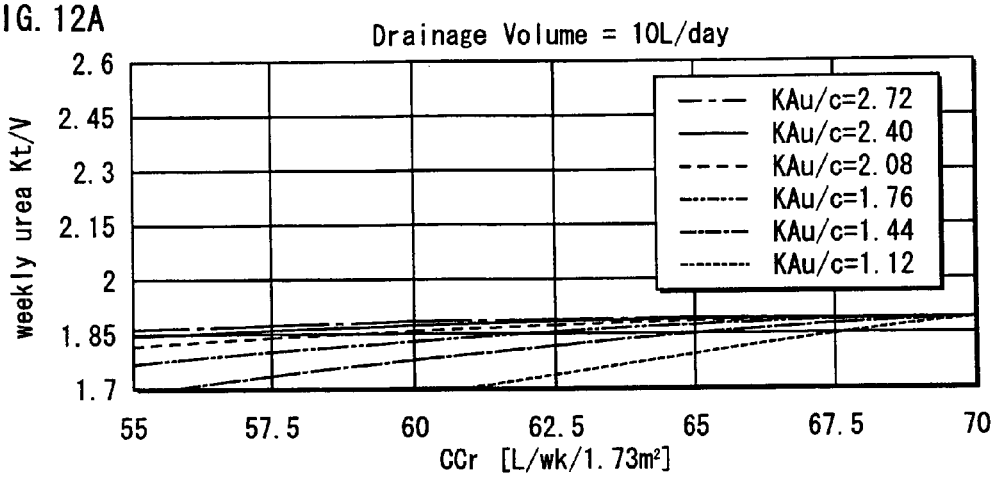
FIG. 12 shows a correlation between Kt/V and CCr.
Figure 12B:
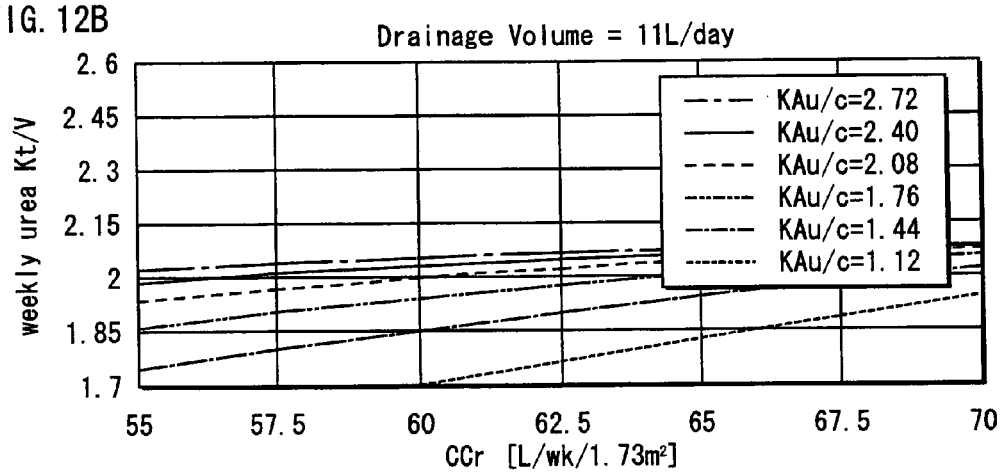
Figure 12C:
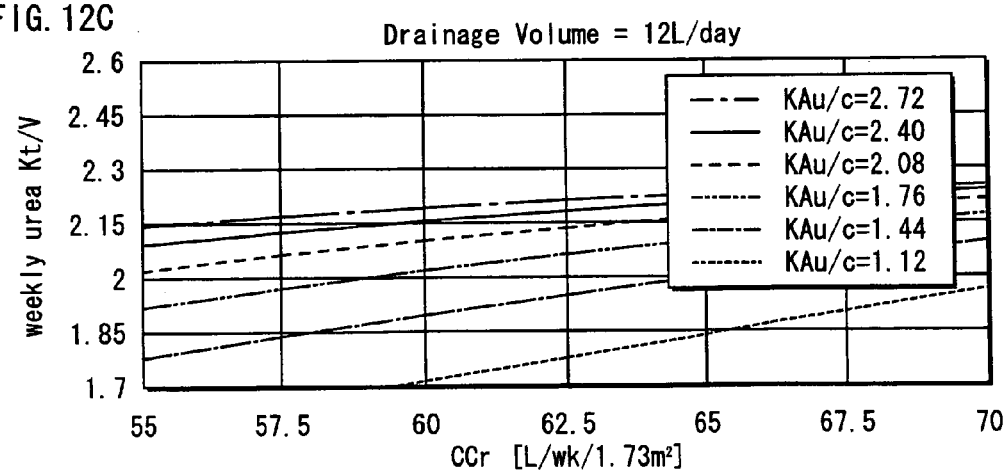
Figure 13A:
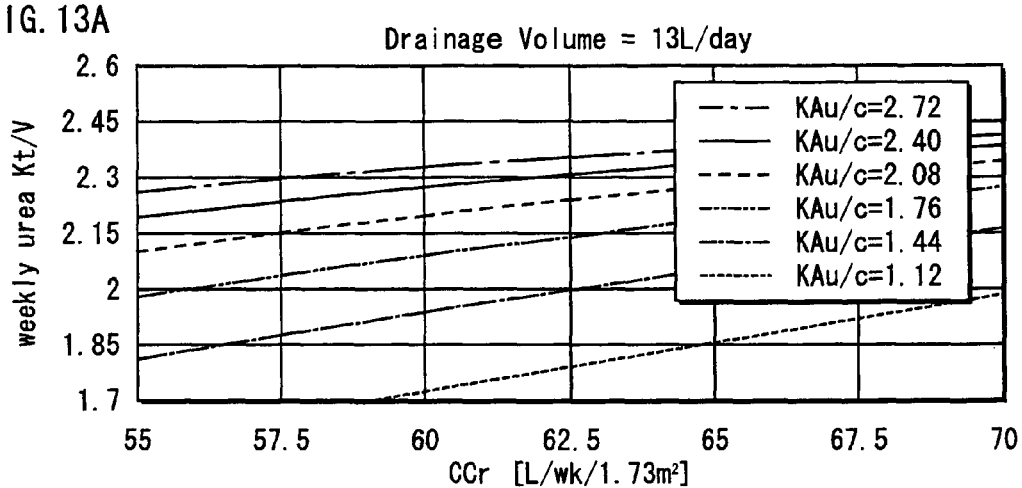
FIG. 13 shows the correlation between Kt/V and CCr.
Figure 13B:
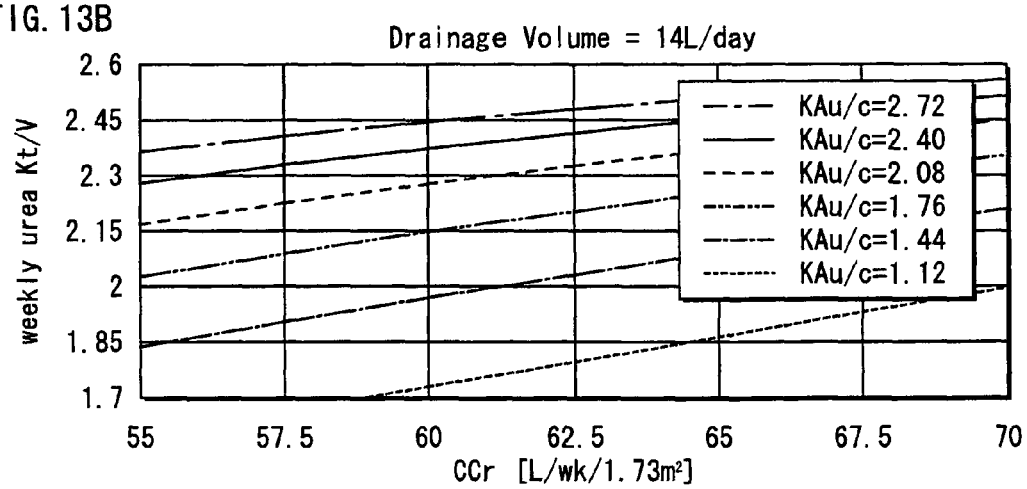

As shown FIGS. 12 and 13, CCr and Kt/V increase as the drained fluid volume increases, irrespective of $MTAC_u/_c$. However, it can be observed that the lower $MTAC_u/_c$ is, the lower CCr and Kt/v are. For instance, in a case where peritoneal function has deteriorated considerably with $MTAC_u/_c=1.12$, even with the daily drained-fluid-volume of 14 L (FIG. 13B), it is difficult to achieve CCr=55 L/week/1.73 m² and weekly Kt/V=1.7 solely with peritoneal dialysis. Accordingly, it can be observed that it is impossible to satisfy the criteria for CAPD adequacy in accordance with the NKF-DOQI guideline (CCr>60 L/week/1.73 m² and weekly Kt/V>2.0).

The conventional PET results, however, are unlikely to be able to conduct such evaluations shown in FIGS. 12 and 13.

For instance, a case of a patient with $KA_u/_c=2.40$ will be studied here with reference to FIGS. 12A and 12B. While the numerical value of $KA_u/_c$ is the same 2.40, when the drained fluid volume is small with 10 L or so (FIG. 12A), the numerical values are out of the ideal-range of CCr being 60 or more and Kt/V being 2 or more, thus the current treatment cannot be considered appropriate. On the other hand, while with the same $KA_u/_c=2.40$, when drained fluid volume of approximately 11 L is ensured (FIG. 12B), dialysis capability of the patient is within the above-mentioned ideal numerical range, and the current treatment can be evaluated as appropriate.

Such a sensitive peritoneal dialysis evaluation is unlikely to be determined if based only on the conventional PET categorization, and it is considered necessary to take all of the four kinetics parameters (CCr, Kt/V, MTAC, MTAC) into consideration, as in the present invention.

[About Evaluation Method of Present Invention]

Figure 11:
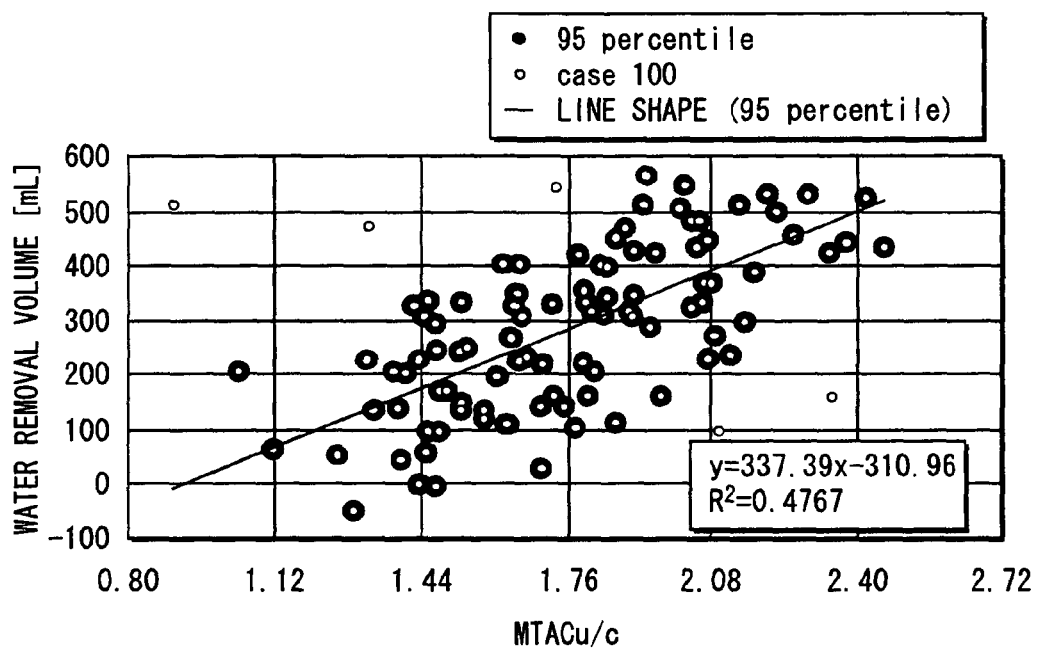
FIG. 11 shows a relationship between $MTAC_u/_c$ for the dialysis solution with the medium osmotic pressure and the drained fluid volume after a 4-hour retention.

FIG. 11 shows a correlation between MTACu/c of the dialysis solution with the medium osmotic pressure and the water removal volume after 4-hour retention.

In the data set (95 percentile), in FIG. 11, which excludes 5 cases out of 100 cases due to a significant deviation from the regression line, $MTAC_u/_c$ and the water removal volume show a desirable correlation ($r^2>0.47$). The molecular weight of the glucose, an osmotic agent, is 180, and the molecular weights of the urea and creatinine are 60 and 113, respectively, showing equal differences among these molecular weights. While it is difficult to calculate MTAC of the glucose due to an effect of metabolism, it is expected, based on the relationship shown in FIG. 9, that MTACs of these molecules are correlated. Accordingly, the results in FIG. 11 are considered to indicate the correlation between $MTAC_u/_c$ and MTAC of the glucose and correlation between $MTAC_u/_c$ and ultrafiltration capability. While MTAC is an index used to define peritoneal permeability, FIG. 11 suggests that MTAC may be applied in the evaluation of the ultrafiltration capability. Conventionally, no index can evaluate both the peritoneal permeability and ultrafiltration capability. However, the present invention suggests that $MTAC_u/_c$ is useful in peritoneal function analysis.

Next, a description will be given along the flow chart in FIG. 4.

First, a curve indicating a relationship of peritoneal function, required effectiveness of dialysis, and the drained fluid volume is obtained by using, as arbitrary reference values, values according to the NKF-DOQI guideline (Kt/V=2.00, CCr=60.0 L/week/1.73 m²), xxx guideline (KT/V=1.85, CCr=57.5 L/week/1.73 m²), and yyy guideline (Kt/V=1.70, CCr=55.0 L/week/1.73 m²) in the formulae (6) and (7) (S101 to S103). The results are shown in FIG. 14.

Figure 14:
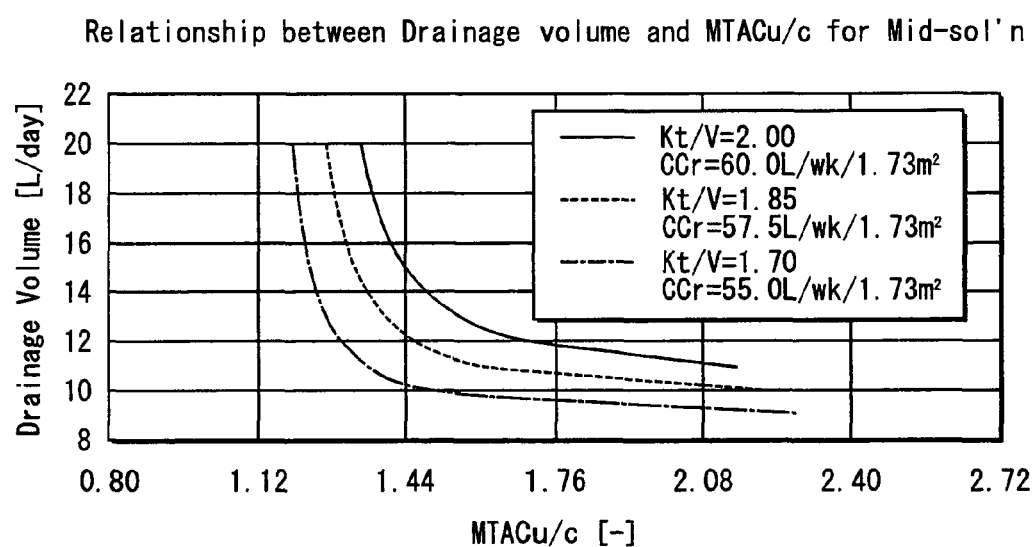
FIG. 14 shows a coordinate system presenting the $MTAC_u/_c$-drained-fluid-volume curve.

According to FIG. 14, when the clinical data is located above these curves, peritoneal dialysis singly can fulfill the required effectiveness of dialysis. Accordingly, A Low transporter of $MTAC_u/_c>1.76$ can achieve these criteria with the drained fluid volume of less than 12 L, indicating that peritoneal dialysis singly can ensure the required effectiveness of dialysis.

Further, by taking into account that a Low transporter has a relatively short history of peritoneal dialysis treatment and retains a residual renal function, FIG. 14 suggests that treatment can be planned without excess use of the dialysis solution with a medium osmotic pressure. Meanwhile, a High transporter of $MTAC_u/_c<1.76$ is evaluated to need to increase the daily drained fluid volume, compared to a Low transporter, in order to ensure the required effectiveness. Especially when $MTAC_u/_c<1.44$ ($MTAC_u/_c<$average value−standard deviation), the effectiveness of dialysis shows a sharp decline, thus the daily drained fluid volume needs to be increased even further.

It should be noted that when the data shown in FIG. 9 was acquired, the water removal volume was 175 ml in a case where $MTAC_u/_c=1.44$ and 2 L of dialysis solution with the medium osmotic pressure was retained for 4 hours. In the case where $MTAC_u/_c=1.44$, even with a severe exchange schedule of 6 exchanges of the dialysis solution with the medium osmotic pressure with each retention period of 4 hours, the daily drained fluid volume is still 13 L, being unable to achieve the criteria of the NKF-DOQI guideline.

As is clear from the above, in the case with $MTAC_u/_c<1.44$, it is expected that the effectiveness of dialysis decline sharply, making it difficult to continue peritoneal dialysis. Accordingly, the treatment policy needs to be revised considerably so as to include, for example, hemodialysis treatment. Thus, considering that change in peritoneal function affects the treatment efficiency more significantly in a case of a High transporter, compared to a case of a Low transporter, conduction of the peritoneal function test is important in improving the prognosis as well.

As can be seen from the above, the present invention exhibits an advantage of providing a dramatically accurate peritoneal function test by enabling a more specific, over-time peritoneal function test compared to conventional evaluation methods.

1-5. Additional Particulars

In the above-mentioned embodiment, as an exemplary case, a dialysis solution with a medium osmotic pressure was used in PET with a 4-hour retention period. Naturally, however, the present invention is not limited to this condition, and a dialysis solution with another osmotic pressure can be used with an appropriate retention period.

Also, the dialysis guidelines can be separately prepared by an operator and the like.

Additionally, the reference values used for the above-mentioned four kinetics parameters can be obtained, instead of directly from the PET results, by performing a simulation using a peritoneal dialysis management software for PC for PET data (for instance, "PDC", an application by Gambro, and "PD ADEQUEST", an application by Baxter).

Further, as disclosed in Japanese Laid-Open Patent Application Publication No. 2005-27886, a hybrid-remedy planning apparatus can be used to manage and compute PET data so as to obtain the reference values.

The present invention is applicable to the study of dialysis planning in peritoneal dialysis and hemodialysis.

The invention claimed is:

1. A peritoneal function testing apparatus, comprising:
a processor;
a memory;
a computation unit having a program recorded therein; and
an output unit configured to output a result of computation by the processor, wherein the program recorded in the computation unit causes the peritoneal function apparatus to perform the following:
a first storing step of storing, in the memory, data obtained by a reference-value substitution for at least two of four parameters of MTACu, MTACc, CCr, and Kt/V;
a first computation step of computing, by the processor, a formula using the four parameters of MTACu, MTACc, CCr, and Kt/V, based on the data stored in the first storing step, so as to obtain an MTACu/c-drained-fluid-volume curve as a computation result;
an output step of outputting, by the output unit, the MTACu/c-drained-fluid-volume curve obtained in the first computation step;
a second storing step of storing, in the memory, the computation result obtained in the first computation step;
a third storing step of storing clinical data in the memory;
a second computation step of computing, by the processor, based on the data recorded in the third storing step the MTACu and MTACc; and
a plotting step of plotting the data obtained in the second computation step based on a result outputted in the output step.

2. The peritoneal function testing apparatus of claim 1, wherein
in the first storing step, (i) the reference-value substitution is performed for the CCr and the Kt/V, and (ii) the formula includes the MTACu/c as a term therein, which is a ratio between the MTACu and the MTACc.

3. The peritoneal function testing apparatus of claim 1, wherein in the first storing step, the formula is a formula (7), $$Kt = V_D \left\{ 1 - \left(1 - \frac{CCr}{V_D}\right)^{MTACu/c} \right\} \quad (7)$$

or a modified formula of the formula (7),
where $V_D$ is a drained fluid volume for a solution with a medium osmotic pressure after a predetermined retention period.

4. The peritoneal function testing apparatus of claim 1, wherein in the first storing step, the formula is a formula (8), $$Kt = V_D \left\{ 1 - \left\{\frac{V_D}{V_D(0)}\right\}^{-n} \left\{ \left\{\frac{V_D}{V_D(0)}\right\}^n \left(1 - \frac{CCr}{V_D}\right) \right\}^{MTACu/c} \right\} \quad (8)$$

or a modified formula of the formula (8),
where n is 0.5 or 1, $V_D$ is a drained fluid volume for a solution with a medium osmotic pressure after a predetermined retention period, and $V_D(0)$ is an injected fluid volume.

5. The peritoneal function testing apparatus of claim 2, wherein the program recorded in the computation unit causes the peritoneal function apparatus to further perform:
an evaluation step of evaluating a relationship between a peritoneal permeability and a drained fluid volume based on results of a peritoneal function test by comparing computation results obtained in the computation step with MTACu/c and the drained fluid volume included in the results of the peritoneal function test, and
wherein in the evaluation step, the computation results and the results of the peritoneal function test are plotted in a coordinate system with the MTACu/c and the drained fluid volume as each axis, and a deterioration of peritoneal function based on the results of the peritoneal function test is predicted in accordance with positions of the plotted results of the peritoneal function test and information obtained from the computation results.

6. The peritoneal function testing apparatus of claim 2, wherein the program recorded in the computation unit causes the peritoneal function apparatus to further perform:
an evaluation step of evaluating a relationship between a peritoneal permeability and a drained fluid volume based on results of a peritoneal function test by comparing computation results obtained in the computation step with MTACu/c and the drained fluid volume included in the results of the peritoneal function test, and
wherein further in the evaluation step, when the results of the peritoneal function test are in such a numerical range that the MTACu/c is 1.44 or lower, a switching point from peritoneal dialysis to hemodialysis or from peritoneal dialysis to a combination of the peritoneal dialysis and the hemodialysis is evaluated by taking into account a scope of the drained fluid volume in the numerical range.

7. A peritoneal function testing apparatus, comprising:
a processor;
a memory;
a computation unit having data and a program recorded therein, the recorded data including an MTACu/c-drained-fluid-volume curve obtained as a result of a computation by the processor according to a formula using four parameters of MTACu, MTACc, CCr, and Kt/V, based on data obtained by a reference-value substitution for at least two of the parameters of MTACu, MTACc, CCr, and Kt/V; and
an output unit configured to output a result of computation by the processor,
wherein the program recorded in the computation unit causes the peritoneal function apparatus to perform the following:
an output step of outputting, by the output unit, the stored MTACu/c-drained-fluid-volume curve in response to an operator's request;
a storing step of storing clinical data in the memory;
a computation step of computing, by the processor, based on the data stored in the storing step the MTACu and MTACc; and
a plotting step of plotting the data obtained in the computation step based on a result outputted in the output step.

8. A non-transitory computer-readable recording medium having recorded thereon a program for a peritoneal function testing apparatus, the apparatus comprising:
a processor;
a memory;
a computation unit having the program stored therein; and
an output unit configured to output a result of computation by the processor,
wherein the program causes the peritoneal function apparatus to perform the following:
a first storing step of storing, in the memory, data obtained by a reference-value substitution of at least two of four parameters of MTACu, MTACc, CCr, and Kt/V;
a first computation step of computing, by the processor, a formula using the four parameters of MTACu, MTACc, CCr, and Kt/V, based on the data stored in the first storing step, so as to obtain an MTACu/c-drained-fluid-volume curve as a computation result;
an output step of outputting, by output unit, the MTACu/c-drained-fluid-volume curve obtained in the first computation step;

a second storing step of storing, in the memory, the computation result obtained in first computation step;
a third storing step of storing clinical data in the memory;
a second computation step of computing, by the processor, based on the data recorded in the third storing step the MTACu and MTACc; and a plotting step of plotting the data obtained in the second computation step based on a result outputted in the output step.

* * * * *